United States Patent [19]
Brain

[11] Patent Number: 5,282,464
[45] Date of Patent: Feb. 1, 1994

[54] COMBINED LARYNGEAL MASK AND REFLECTANCE OXIMETER

[76] Inventor: Archibald I. J. Brain, St. Andrews, Abney Court Drive, Bourne End, Bucks, United Kingdom

[21] Appl. No.: 980,581

[22] Filed: Nov. 23, 1992

[30] Foreign Application Priority Data

Jul. 21, 1992 [GB] United Kingdom ............... 9215455

[51] Int. Cl.⁵ .............. A61M 16/00; A62B 7/00; F16K 31/02; A61B 5/00
[52] U.S. Cl. .............. 128/207.15; 128/204.22; 128/633; 128/634
[58] Field of Search ............ 128/207.14, 204.22, 128/207.15, 205.23, 786, 787, 911, 912, 204.18, 633, 634, 664–666; 606/2, 14; 356/41

[56] References Cited

U.S. PATENT DOCUMENTS

| | | | |
|---|---|---|---|
| 3,640,282 | 2/1972 | Kamen et al. | 128/207.15 |
| 3,866,599 | 2/1975 | Johnson | 128/634 |
| 4,399,820 | 8/1983 | Wirtzfeld et al. | 128/633 |
| 4,444,185 | 4/1984 | Shugar | 128/634 |
| 4,509,514 | 4/1985 | Brain | 128/207.15 |
| 4,621,643 | 11/1986 | New, Jr. et al. | 128/633 |
| 4,995,388 | 2/1991 | Brain | 128/207.14 |
| 5,005,573 | 4/1991 | Buchanan | 128/634 |
| 5,103,814 | 4/1992 | Maher | 128/204.18 |
| 5,193,544 | 3/1993 | Jaffe | 128/207.14 |
| 5,205,281 | 4/1993 | Buchanan | 128/207.14 |

Primary Examiner—J. Reed Fisher
Assistant Examiner—Kimberly L. Asher
Attorney, Agent, or Firm—Hopgood, Calimafde, Kalil, Blaustein & Judlowe

[57] ABSTRACT

A reflectance oximeter is so mounted to the upstream or proximal side of a laryngeal mask as to face the posterior wall of the pharynx when the laryngeal mask has been positioned to perform its function of sealed, exclusive airway communication with the laryngeal inlet. Thus positioned, radiation from the oximeter can utilize local back-bone features as a reflector, for two-way passage of the radiation through tissue which characterizes the posterior wall of the pharynx. Moreover, the oximeter-observation region is within the body, so that ambient light has no degrading effect, and changes in oxygen saturation will be detected earlier than by use of any peripherally placed oximeter probe.

28 Claims, 3 Drawing Sheets

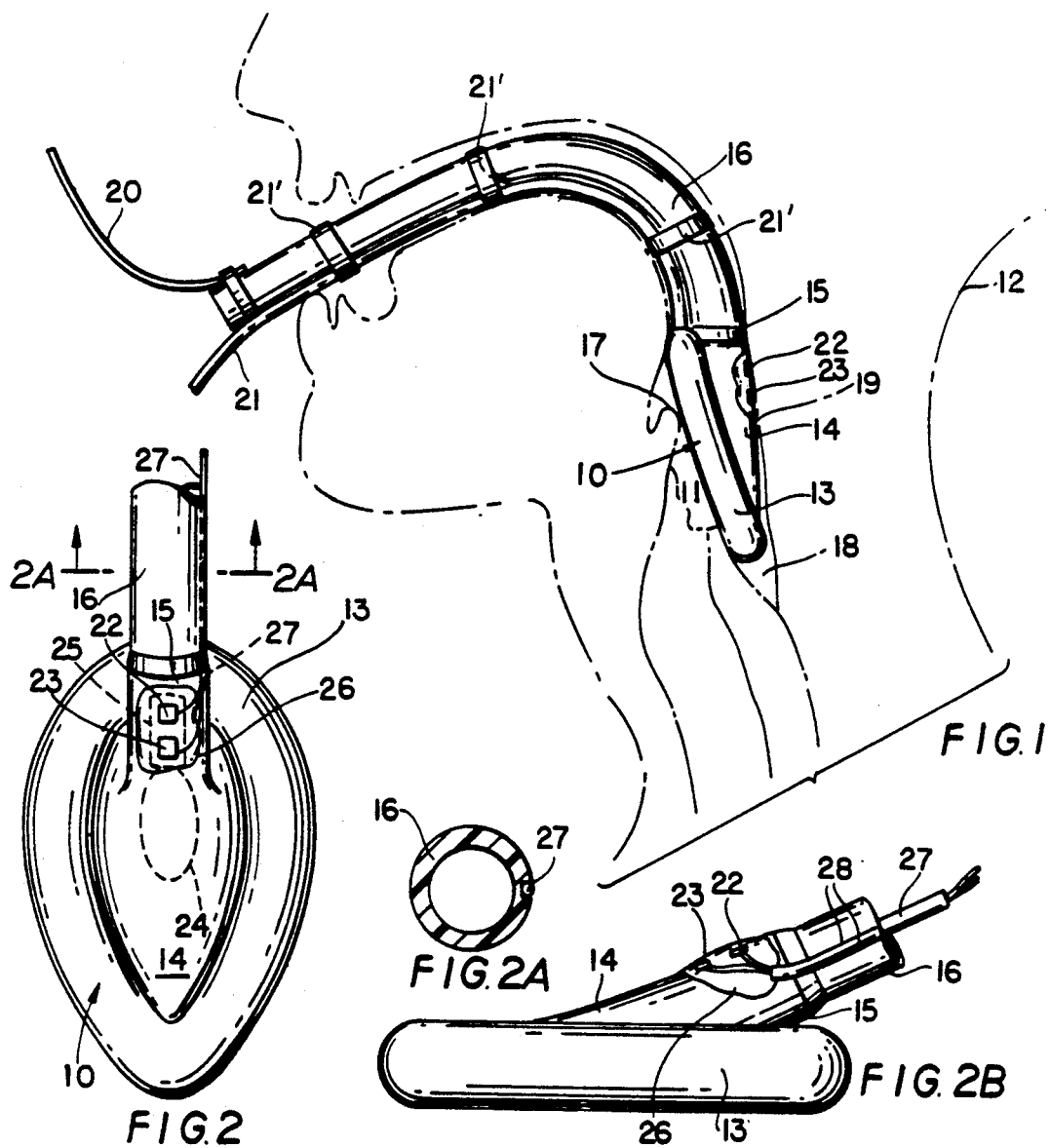
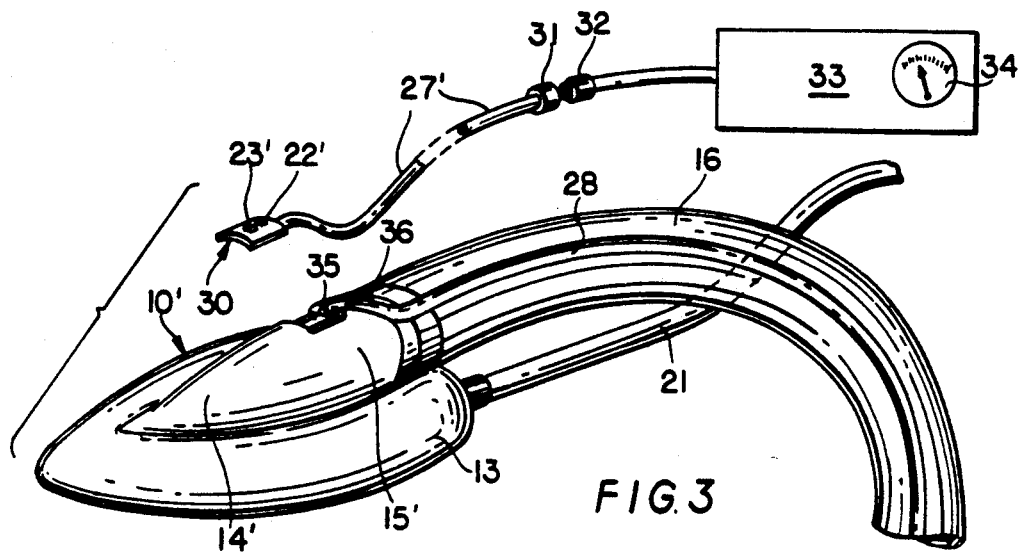

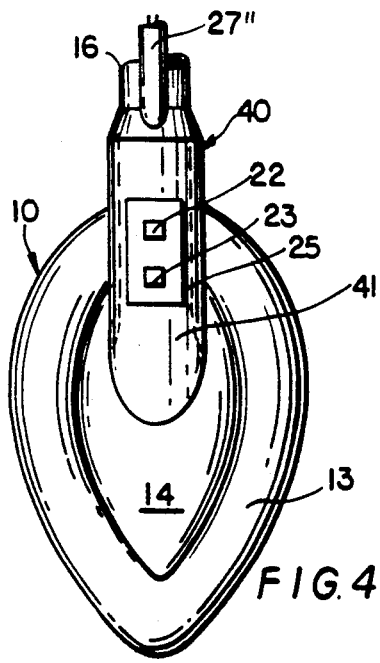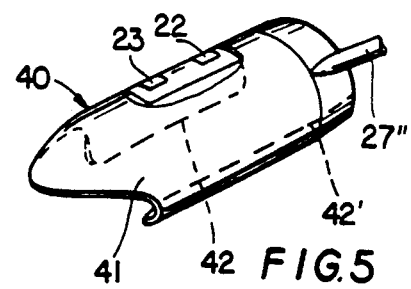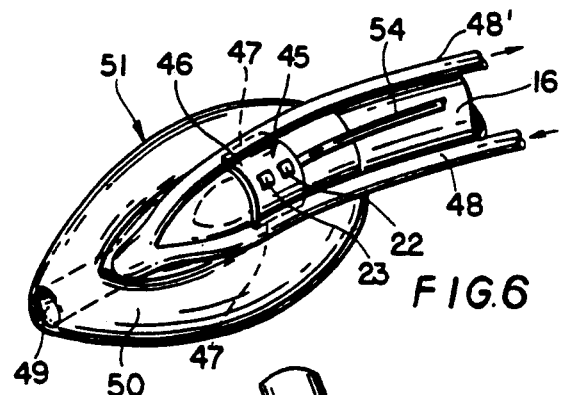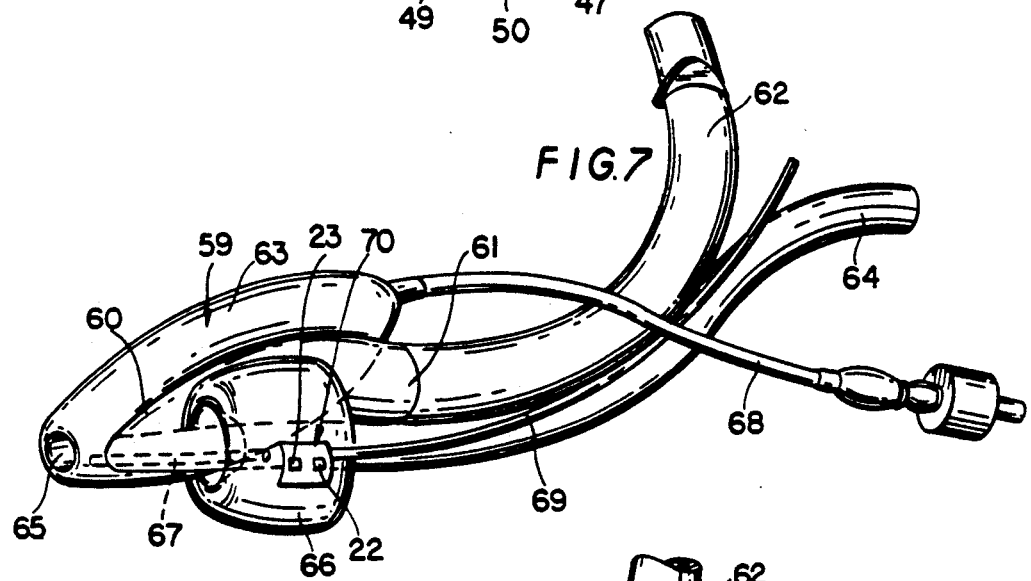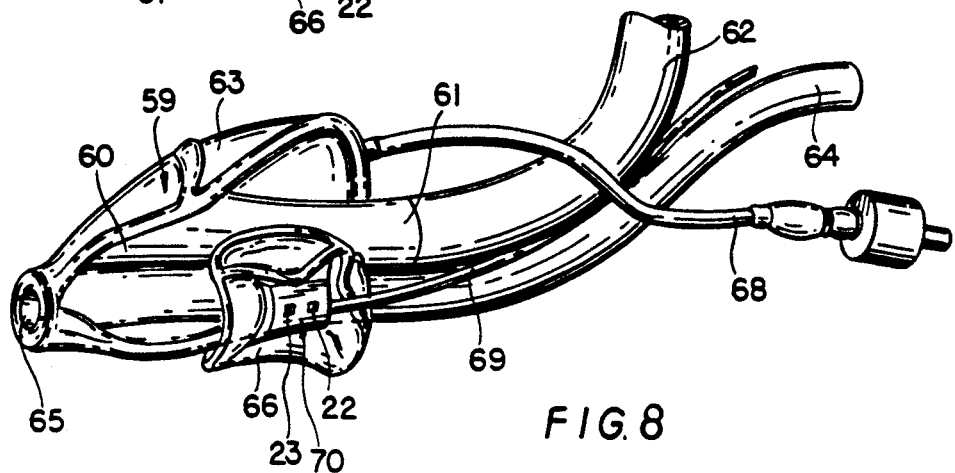

COMBINED LARYNGEAL MASK AND REFLECTANCE OXIMETER

BACKGROUND OF THE INVENTION

The invention relates to laryngeal mask airway devices for facilitating lung ventilation in an unconscious patient and to the coordinated use therewith of a reflectance oximeter for monitoring oxygenation in the blood as an indicator of current effectiveness of the lung ventilation.

Laryngeal-mask devices have been described in my U.S. Pat. Nos. 4,509,514 and 4,995,388, as well as in my copending U.S. patent applications, Ser. No. 919,289 filed Jul. 24, 1992, and Ser. No. 952,586 filed Sep. 28, 1992, which are incorporated herein by reference.

Such masks are artificial airway devices designed to facilitate lung ventilation in an unconscious patient by forming a low-pressure seal around the laryngeal inlet. A seal surrounds an appropriately shaped mask which fits into the lower pharynx and is attached to an airway tube which emerges from the mouth, as for connection to medical gas-supply tubing.

Such masks are artificial airway devices designed to facilitate lung ventilation in an unconscious patient by forming a low-pressure seal around the laryngeal inlet. A seal surrounds an appropriately shaped mask which fits into the lower pharynx and is attached to an airway tube which emerges from the mouth, as for connection to medical gas-supply tubing. More specifically the mask may comprise a plate with an inflatable ring having peripherally sealed engagement to the laryngeal inlet; and an elongate airway tube has a distal end that is sealed to the plate, for completing an externally accessible airway passage through the plate, for exclusive airway communication with the laryngeal inlet.

Pulse oximetry is a technique for non-invasively measuring the oxygen level in blood and has proved to be a very useful clinical tool as a means of continuously assessing the adequacy of ventilation, particularly in anaesthetized patients, for whom adequate oxygenation is a key concern. Most commercial pulse oximeters measure the signal when light of appropriate wavelengths is shone through a tissue such as a finger, and there are now more than 30 manufacturers of such devices. However, there are disadvantages to this technique, the most important being that the finger probe may easily become detached during use, with loss of signal, perhaps at a critical moment; also, since the device is peripheral in position, there is sometimes poor correlation between blood oxygenation in the finger, and oxygenation where it matters most—for example in the brain. Attempts to rectify this have resulted in development of probes for use on the ear, eyelid, and nose, with varying degrees of success.

Another approach has been to develop a related technique, reflectance oximetry, which has been described theoretically by Cui, Ostrander and Lee ("In Vivo Reflectance of Blood and Tissue as a Function of Light Wavelength", IEEE Transactions on Biomedical Engineering, 1990, vol. 37, no. 6: 632 to 639) and in certain practical applications[1]. The aim is to measure a signal reflected back from a tissue surface instead of having to rely on light transmission. This avoids the necessity of using peripheral tissues such as the finger, since tissue thickness is no longer a problem. The disadvantages of the reflectance oximeter are that accuracy is reduced, in that there may be problems with incident light, and it may be necessary to heat the skin in order to maximize blood flow in the skin, noting that skin is always at a lower temperature than blood.

[1] See for example:
Cheng, Hopwood and Kay, "Forehead Pulse Oximetry Compared with Finger Pulse Oximetry and Arterial Blood Gas Measurement", Journal of Clinical Monitoring, 1988, vol. 4, no. 3: 223 to 226.
Mendelson and McGinn, "Skin Reflectance Pulse Oximetry: In Vivo Measurements from the Forearm and Calf", Journal of Clinical Monitoring, 1991, vol. 7, no. 1: 7 to 12.
Mendelson and Ochs, "Noninvasive Pulse Oximetry Utilizing Skin Reflectance Photoplethysmography", IEEE Transactions on Biomedical Engineering, 1988, vol. 35, no. 10: 798 to 805.
Johnson, Johnson, Fisher, Jobbings, Bannister, and Lilford, "Fetal Monitoring with Pulse Oximetry", British Journal of Obstetrics and Gynaecology, 1991, vol. 98: 36 to 41.

BRIEF STATEMENT OF THE INVENTION

It is an object of the invention to so combine a reflectance oximeter with a laryngeal-mask airway as to avoid the above-noted disadvantages of conventional pulse oximetry and reflectance oximetry.

Another object is to achieve the above object in a unitary device such that established procedures with insertion, operation and removal of a laryngeal mask are not affected by concurrent oximeter presence and operation.

A further object is to provide a structure whereby reflectance-oximeter operation may be selectively added to an existing laryngeal mask.

A general object is to achieve the above objects with relatively simple and inexpensive apparatus, that can be correctly installed, operated and removed by relatively unskilled personnel, without inducing patient trauma.

The invention achieves the foregoing objects by so mounting a reflectance oximeter to the upstream or proximal side of a laryngeal mask as to face the posterior wall of the pharynx when the laryngeal mask has been positioned to perform its function of sealed, exclusive airway communication with the laryngeal inlet. Thus positioned, radiation from the oximeter can utilize local back-bone features as a reflector, for two-way passage of the radiation through tissue which characterizes the posterior wall of the pharynx. Moreover, the oximeter-observation region is within the body, so that ambient light has no degrading effect, and changes in oxygen saturation will be detected earlier than by use of any peripherally placed oximeter probe.

BRIEF DESCRIPTION OF THE DRAWINGS

The invention will be described in detail for each of several embodiments, in conjunction with the accompanying drawings, in which:

FIG. 1 is a view in side elevation showing a laryngeal mask system including an oximeter, with phantom outlines to show features of the head of a patient in whom the mask has been installed;

FIG. 2 is an enlarged posterior-aspect view of the mask of FIG. 1;

FIG. 2A is a section taken at 2A—2A in FIG. 2;

FIG. 2B is a view in side elevation of the mask of FIG. 2;

FIG. 3 is a simplified view in perspective of a modified mask system, generally as in FIG. 1, but with an oximeter-subassembly in exploded readiness for assembly to the mask;

FIG. 4 is a posterior-aspect view of another modification, wherein a mount for an oximeter is selectively adaptable for and is shown assembled to a laryngeal mask of existing construction;

FIG. 5 is a perspective view of the oximeter and mount of FIG. 4, separate and apart from the mask of FIG. 4;

FIG. 6 is a perspective view of a modified laryngeal mask and oximeter;

FIG. 7 is a perspective view of a further modified laryngeal mask and oximeter;

FIG. 8 is a view similar to FIG. 7, for the deflated condition of the inflatable components of FIG. 7;

DETAILED DESCRIPTION OF THE INVENTION

Figure 9:
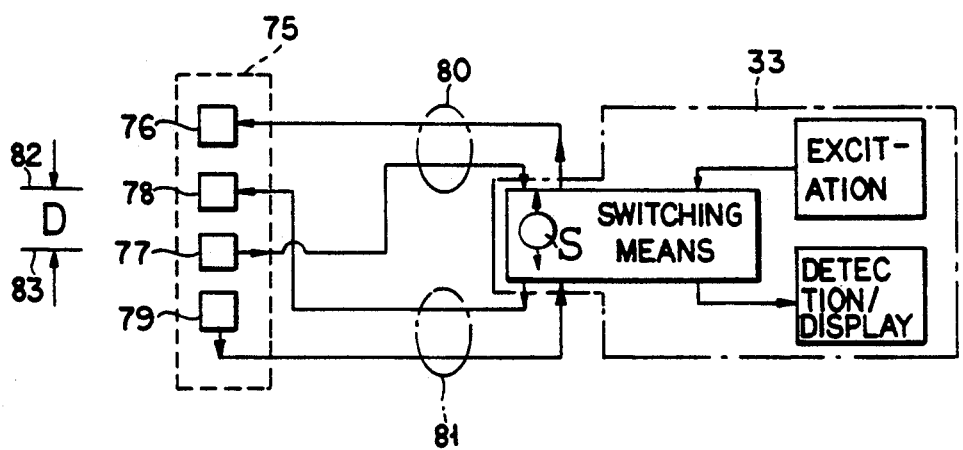
FIG. 9 is a schematic layout of multiple diodes for a modified oximeter-probe portion of a laryngeal mask.

In the installed system of FIG. 1, a laryngeal mask 10 has peripherally sealed engagement around the laryngeal inlet 11 of a patient 12. Thus sealed, the mask 10 presents a front (or anterior) side facing into the laryngeal inlet, and a back (or posterior) side facing the back wall of the pharynx. The sealed engagement is via an air-inflated annular ring 13 which is connected to and supports a central plate 14 having an inlet airway port formation 15 on a sloping alignment with respect to the general plane of ring 13. An airway tube 16 is connected at its distal end to the port formation 15 and is curved for general conformance with the patient's natural breathing passage via the throat to the pharynx. As shown, the seal to the laryngeal inlet surrounds the epiglottis 17 and has a sealed footing at the oesophageal inlet 18; also, the slope of the airway port formation 15 conforms generally with tissues along the posterior wall 19 of the pharynx. The airway tube 16 may be rigid or stiffly flexible, and a manipulating handle 20 is shown at the outer end of tube 16, for facilitating mask insertion into the patient, with the ring 13 in deflated condition, the inflation/deflation procedure being externally controllable via an inflation-air supply tube 21. The particular mask 10 of FIG. 1 will be understood to be an illustrative one of several varieties,, greater detail of which will be found in various of the above-identified patents and patent applications. For reference purposes, the front or anterior side of mask 10 will be understood to be the side which faces the laryngeal inlet and passage, and the back or posterior side of mask 10 will be understood to be the side which faces the posterior or back wall 19 of the pharynx.

In accordance with a feature of the invention, oximeter instrumentation is built into or otherwise carried by the mask 10, whereby to enable continuous monitoring of the oxygen content of blood supplied to the brain while also controlling and monitoring air and/or anaesthetic supply to the patient via the tube 16 and mask. In FIG. 1, a suggestion of the added oximeter feature appears at the longitudinally spaced diodes 22, 23 which are adhered to the posterior of plate 14, in the region near the air-inlet port formation 15. External wiring which serves diodes 22, 23 has been omitted from FIG. 1 but will be understood to be preferably retained to or alongside airway tube 16, as by the spaced straps 21' which are shown performing the analogous function for inflation tube 21.

Better detail for oximeter instrumentation 22, 23 will be evident from FIGS. 2, 2A and 2B, wherein the inflated annular ring 13 is seen to be generally elliptical, with a somewhat pointed distal end, for locating and sealing engagement at the oesophageal inlet. In the plan view of FIG. 2, plate 14 is seen to provide an opening 24 in its anterior side for airway communication via tube 16 and formation 15 to the laryngeal inlet. The diodes 22 and 23 may be as provided by Nellcor Incorporated (Foster City, San Francisco, Calif.) for their pulse oximeter Model 200, which is commercially available complete with its power supply, signal-generator and reflected-signal detector and flexible cabling for sufficiently remote connection to the diodes 22, 23, one (22) of these diodes is an LED emitting in the red end of the visible spectrum, while the other (23) is a photodetector diode. In application of such diodes to the present situation, they are advisedly mounted to a thin bed 25 of light absorbing material such as an elastomeric that has been mixed with carbon black to render the same opaque, and this material should be built to greatest thickness between diodes 22, 23, so as to minimize direct coupling of light from the LED to the photodetector. The overall maximum thickness for the diodes in their assembly to each other via a bed 25 is in the order of 2 mm, which is a minimal increase in overall profile for plate 14 and its inlet formation 15; the bed 25 may be cemented to formation 15, and an application 26 of self-leveling, optically transparent silicone is sufficient to cover the cemented combination, as well as otherwise-exposed individual insulated electrical leads and cable-sheathing 27 therefor.

As shown in FIGS. 2A and 2B, it is preferred that the tubing of airway 16 shall be formed with an elongate outwardly open channel 28 for retaining cable 27; the confronting outer edges of this channel 28 are seen in FIG. 2B to be spaced less than the diametral extent of cable 27, thus enabling the cable to be frictionally retained by and to tube 16.

In the embodiment of FIG. 3, the diode or probe unit 30 of oximeter apparatus is a separate article of manufacture, complete with its flexible cabling 27' to an external connector element 31. A second, mating, detachable-connector element 32 is part of a suitable cabinet or housing 33 for signal-generator, signal-processing and display means 34 for monitoring oxygen content of blood observed by the diodes 22', 23' of unit 30. Unit 30 is shown as a thinly developed arcuate block, as of epoxy and having the blackened light-absorbing feature noted above for the devices 22, 23 of FIG. 2 and their mounting 25. The laryngeal mask 10' of FIG. 3 will be seen at its region 15' to have been formed with a shallow arcuate recess 35 adapted for removable insertion and retention of diode unit 30, and a shallow groove 36 in the plate-body region 15' communicates with the cable-retaining groove 28 of the airway tube 16, to assure full reception and location of cable 27' all the way from recess 35 to the external region of coupling 31, 32 to the housing 33 of requisite electronics and controls.

In the arrangement of FIGS. 4 and 5, the unit 40 of FIG. 5 is also part of a unitary assembly of oximeter-probe components, namely, diode elements 22, 23 locally mounted as previously described, except that the mount 41 is a cylindrically arcuate member which carries the diodes centrally of its upper surface, while its spaced arcuate ends 42, 42' must be compliantly spread in order to be fitted to the customary generally cylindrical profile of the inclined airway-connecting end formation (15) of the mask plate 14. The mount 41 may be of relatively stiff plastic material, or of a relatively softly yieldable plastic material which carries an imbedded cylindrically arcuate stainless-steel spring member (not shown), or the entire mount 41 may be of stainless steel, arcuately formed for clinging, compliantly stressed, retaining engagement to the plate formation 15. Thus, the arrangement of FIGS. 4 and 5 represents a form of the invention which is removably attachable to an existing laryngeal mask, without requiring any change in the construction of the mask itself.

In the embodiment of FIG. 6, a separate unitary oximeter-probe assembly 45 of diodes 22, 23 includes a cylindrically arcuate base 46 with side flanges 47 that removably engage under bifurcated conduit arms 48, 48' for a continuously flowing fluid, such as water or air, or an air/water mixture, for aspirating products of regurgitation from the oesophagus, and entering a passage 49 through the inflatable ring 50 of a laryngeal mask 51. An in-flow directional arrow in connection with conduit arm 48 and an out-flow directional arrow in connection with conduit arm 48 will be understood to suggest the continuous flow of fluid. Such mask structure is described in greater detail in my patent application Ser. No. 952,586 and therefore needs no present elaboration. It suffices merely to identify the means 48, 48' of such aspiration, piggy-backed to the plate structure 52 and straddling the inclined inlet-port formation 53 of the mask, and to indicate that the probe unit 45 and its flexible-lead cable 54 may be selectively applied to the mask 51.

The mask arrangement of FIGS. 7 and 8 is of another variety described in detail in said pending patent application, Ser. No. 952,586. It suffices merely to identify the mask plate 60, its inclined air-inlet port formation 61 (with connected airway tube 62), and its peripherally continuous, elliptically annular inflatable ring 63 for sealed engagement to the laryngeal inlet. A vacuum (i.e., reduced pressure) conduit 64 is piggy-backed to the airway tube and communicates with an opening 65 at the distal end of ring 63, for vacuum extraction and removal of possible products of regurgitation, entering from the oesophagus via opening 65. As disclosed in said Ser. No. 952,586, a second inflatable/deflatable balloon or cuff 66 surrounds the exposed periphery of conduit 64 at its region of generally central overlap with the mask plate 60 and its inclined air-inlet port formation 61. A single air inflation/deflation line 68 has direct communication with the inflatable laryngeal-seal ring 63 and indirect further communication (via a passage 67, between ring 63 and cuff 66). And a cylindrically arcuate oximeter-probe assembly 70 with spaced diodes 22, 23 is simply adhered to the exterior of cuff 66, in such manner that upon inflation of ring 63 and cuff 66, not only does cuff 66 establish a contour-adapting and stabilizing engagement to the posterior wall of the pharynx (in reacting pressure-loading enhancement of the laryngeal-inlet seal established by the inflated mask ring), but the oximeter-probe unit 70 carried by cuff 66 is firmly applied to the pharyngeal wall, in direct confrontation with the thin tissue of this wall and in relatively closely spaced confronting relation with adjacent vertebra structure that is relied upon for the reflection involved in pulse reflection oximetry.

FIG. 8 serves to illustrate that upon deflation of ring 63 and cuff 66, not only do the mask 59 components reduce to floppy unimpeding significance, but in addition the oximeter-probe unit 70, being preferably cylindrically arcuate, is drawn into close and nested proximity to the evacuation tube 64, thus presenting no impediment to safe insertion or removal of the mask (with its oximeter-probe unit 70) with respect to its intended situs within the pharynx. Neither does the flexible cabling 69 which serves unit 70 present any difficulty for such insertion or removal of the mask and its oximeter-probe unit.

In all of the described embodiments, the oximeter probe has been indicated as involving two diodes, one (22) an LED, and the other (23) a photodiode. Suitable diodes for the indicated purpose are not necessarily square (as schematically shown in the drawings), but their operative areas are in the order of 2 to 4-mm span in their maximum dimension, and it is recommended that they be mounted at approximately 10-mm spacing (center-to-center). Neither is the longitudinally spaced relation of these diodes necessarily to be preferred, in that optimum results and operation result from good LED radiation through thin pharyngeal tissue thickness and general directional orientation to a good reflecting vertebral surface which will reflect maximally to the photodiode; such criteria can also be satisfied by a strictly transverse spacing of the diodes 22, 23. Also, as indicated by a diode array schematically indicated in FIG. 9, the chances of getting better oximeter performance in any given one of plural patients are improved if an additional two diodes are mounted to their common base 75, in spaced and interlaced array. Thus, in FIG. 9, a first pair of diodes (i.e., an LED 76 and its associated photodiode 77), at the recommended center-to-center spacing, may be in longitudinally aligned interlace with a second pair of diodes (i.e., an LED 78 and a photodiode 79). Each coacting pair of diodes may have its own separate lead connections 80 (81) for accommodation in the flexible-cable tie to the external electronics housing, such as housing 133 of FIG. 3; and for the convenience of the attending anaesthetist, a manual switchs may be available for his quick selection as to the diode pair to be used for best oximeter performance in a given case. The longitudinal center served by selection of diodes 76, 77 is indicated at 82, and the longitudinal center served by selection of diodes 78, 79 is indicated at 83.

It will be seen that the described embodiments of the invention meet the above-stated objects and also provide certain specific advantages, including the following:

1. In the United Kingdom, where the laryngeal mask and the pulse oximeter (attached to a finger or toe) are both widely used in general anaesthesia, they are frequently in use at the same time. Attachment of the oximeter to the laryngeal mask therefore eliminates an additional "line" attaching the patient to the anaesthetic trolley, since the cable from the oximeter can follow or even be incorporated in the airway line joining the laryngeal mask to the gas outlet. (There are no explosion hazards with modern anaesthetics). The common problem of a probe being pulled off or falling off a finger or toe is thus eliminated.

2. The laryngeal mask is situated in the deepest part of the throat, therefore an oximeter probe attached in this position will pick up signals of much more relevance to key areas of concern, such as the brain. Moreover, changes in oxygen saturation will be detected earlier than by use of any peripherally placed oximeter probe.

3. The central position of the oximeter probe and the fact it is in contact with mucosa (lining of the throat) instead of skin both increase the likelihood of obtaining high quality signals, since in the throat, temperature is not significantly different from that of the blood—thus, no warming is necessary—and the mucosal blood vessels are in any case closer to the surface.

4. Ambient light interference is no longer a problem, thus eliminating this source of innaccuracy.

5. A further advantage of combining the two devices derives from a unique property of the laryngeal mask: it is the only effective airway device which can safely be left in place in the unconscious patient until full recovery occurs. Now it is well known that many problems with breathing (and thus with oxygen uptake) occur during the period of recovery from anaesthesia. An oximeter probe which reliably stays in place during transfer of the patient from operating room to recovery area and maintains constant monitoring until the patient is safely recovered would be much appreciated by anaesthetists and recovery staff.

6. Finally, again in the recovery phase, two factors commonly cause problems with existing peripherally placed oximeter probes: patients may be restless, causing displacement of the probe; and peripheral blood-vessel shut-down may occur associated with shivering, blood-loss, or pain. Neither of these factors is likely to present a problem with the present invention.

Figure 10:
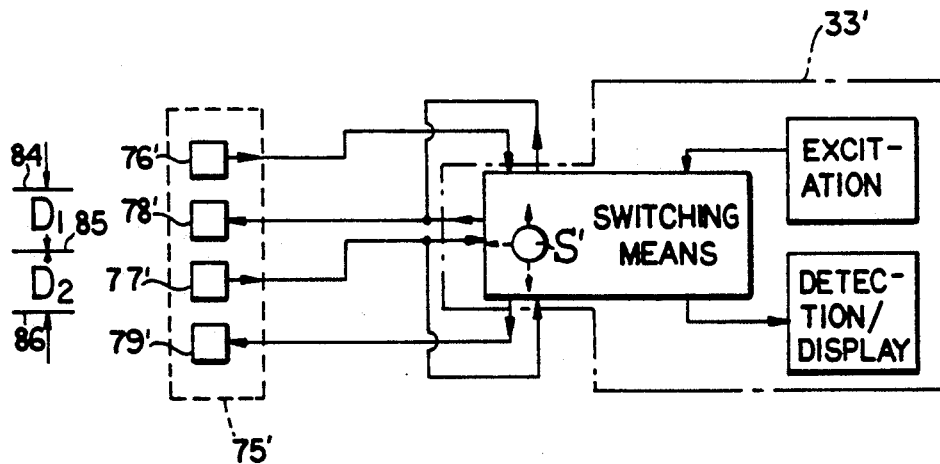
FIG. 10 is a diagram similar to FIG. 9, for a modified layout.

In connection with FIG. 9, the plural diodes 76, 78, 77, 79 were described in longitudinally spaced array, so as to make available the selection of a given pair (76, 78, or 77, 79) for best reflectance; the longitudinal selection thus available with selection of one or the other of these pairs may be the distance D, shown on the drawing. The same or a similar array will also be seen in FIG. 10 to provide further alternatives for switching selection at external electronics 133. For example, if diode 78 is an LED, flanked proximally and distally by photodiodes 76, 77, switchable oximeter selection of diodes 76, 78, or of diodes 77, 78 will provide a longitudinal oximeter probe selection as between two spaced locations. The longitudinal center served by selection of diodes 76', 78' is indicated at 84; the longitudinal center served by selection of diodes 77', 78' is indicated at 85; and the longitudinal center served by selection of diodes 77', 79' is indicated at 86. The selection of one to the exclusion of another of the longitudinal oximeter locations in FIG. 10 may be by manual switch operation at 133; alternatively the selection may be automatic via periodic sampling of the respective alternative oximeter pairs, wherein the samplings are automatically evaluated and switching is automatically effected by known electronic techniques and circuitry, a of which will be understood to be contained within means 133, 133' when connected to leads for optional pairs of diodes, such as shown and discussed in connection with FIGS. 9 and 10.

What is claimed is:

1. In combination, a laryngeal mask having a front side and a back side and means for establishing peripherally sealed engagement of said mask around the laryngeal inlet of a patient, with the front side facing into the laryngeal inlet and the back side facing the back wall of the pharynx, an elongate airway tube having a distal end which establishes a sealed passage through said mask between the back and front sides of said mask, and reflectance-oximeter probe means carried at the back side of said mask and oriented to radiate into and to sense radiation reflected from within a localized portion of the back wall of the pharynx.

2. The combination of claim 1, in which said mask comprises a plate via which said airway tube has sealed communication with said passage, and in which said plate includes a recess formation with said oximeter probe means carried in the recess formation.

3. The combination of claim 2, in which said oximeter probe means is removably carried in the recess formation.

4. The combination of claim 2, in which said oximeter probe means includes a flexible cable for establishing external electrical connection to source of excitation signals for oximeter-detected signals, and in which said airway tube has an elongate groove formation adapted to removably retain said cable.

5. The combination of claim 1, in which said means for establishing sealed mask engagement around the laryngeal inlet is an inflatable annular ring, and in which said oximeter probe means is carried by said mask at a location which, in plan view is radially within the annulus of said ring.

6. The combination of claim 1, in which said oximeter probe means is fixedly carried by the back side of said mask.

7. The combination of claim 1, in which said oximeter probe means is removably carried by the back side of said mask.

8. The combination of claim 1, in which said mask includes an inflatable cuff at the back side of the mask for development of distributed-area contact with the back wall of the pharynx, and in which said oximeter probe means is carried by said cuff within the region of cuff contact with the back wall of the pharynx.

9. The combination of claim 8, in which said means for establishing sealed mask engagement around the laryngeal inlet is an inflatable annular ring, and a single flexible tube for communicating inflation air is connected for concurrent inflation of said cuff and of said annular ring.

10. The combination of claim 1, in which said oximeter probe means includes a flexible cable for establishing external electrical connection to source of excitation signals for oximeter radiation and to a processor of oximeter-detected signals.

11. The combination of claim 10, in which said airway tube has an elongate local groove formation adapted to removably retain said cable.

12. The combination of claim 1, in which said oximeter probe means comprises an LED diode in spaced proximity to a photodetector diode.

13. The combination of claim 12, in which the spacing of said diodes is in the longitudinal direction of airway-tube connection to said mask.

14. The combination of claim 1, in which said oximeter probe means comprises plural spaced pairs of spaced diode elements, wherein each pair comprises an LED diode and a photodetector diode.

15. The combination of claim 14, wherein electronic circuitry is selectively and remotely switch-connected to one to the exclusion of other pairs of said plurality.

16. The combination of claim 1, in which said oximeter probe means comprises an array of spaced diodes wherein each of two opposite sides of an LED diode is flanked by a photodetector diode.

17. The combination of claim 16, wherein electronic circuitry is selectively and remotely switch-connected to one to the exclusion of said photodetector diodes while said circuitry is continuously connected to said LED diode.

18. In combination, a laryngeal mask comprising a plate having a front side and a back side and means including an inflatable annular ring peripherally connected to said plate in essentially a single plane for establishing peripherally sealed engagement of said mask around the laryngeal inlet of a patient, with the front side facing into the laryngeal inlet and the back side facing the back wall of the pharynx, the back side of said plate having a tubular airway inlet formation on an alignment which rises from said plane at an acute angle, an elongate airway tube having a distal end which establishes via said inlet formation a sealed passage through said mask between the back and front sides of said mask, and reflectance-oximeter probe means carried by the inlet formation of said mask and oriented to radiate into and to sense radiation reflected from within a localized portion of the back wall of the pharynx.

19. The combination of claim 18, in which said inlet formation includes a recess formation with said oximeter probe means carried in the recess formation.

20. The combination of claim 18, in which said oximeter probe means is fixedly carried by said inlet formation.

21. The combination of claim 18, in which said oximeter probe means is removably carried by said inlet formation.

22. The combination of claim 21, in which said oximeter probe means is mounted to the convex surface of a cylindrically arcuate shell configurated for compliantly stressed retaining engagement to said tubular inlet formation.

23. The combination of claim 18, in which said mask includes an inflatable cuff at the back side of the mask and engaged to said inlet formation for development of distributed-area contact with the back wall of the pharynx, and in which said oximeter probe means is carried by said cuff within the region of inflated-cuff contact with the back wall of the pharynx.

24. The combination of claim 23, in which a single flexible tube is connected for communicating inflation air for concurrent inflation of said cuff and of said annular ring.

25. An artificial airway device to facilitate a patient's lung ventilation, comprising an airway tube, an evacuation tube, and a laryngeal mask at one end of said tubes, said mask including a first inflatable-cuff formation of flexible material in a generally elliptical configuration extending from a proximal end to a distal end and in generally a single plane which is inclined to the axis of the airway tube at the distal end of the airway tube, a second inflatable-cuff formation carried by said mask on the posterior side of said plane, said mask being configured upon inflation of said cuff formations (1) to form a seal of said airway tube solely around the circumference of the laryngeal inlet and (2) to establish a cushioning action via said second cuff formation between the posterior side of said mask and the posterior wall of the pharynx, the distal end of said first cuff formation being configured for entry into and insertional location of said device by engagement with the oesophagus at the upper sphinctral region of the oesophagus when the mask is positioned for sealing the airway tube to the laryngeal inlet, said evacuation tube having an open distal end centrally within and axially short of the distal end of said first cuff formation, inflation-passage means communicating with both said inflatable cuff formations for selective inflation/deflation operation of said cuff formations; said cuff formations, upon inflation via said inflation-passage means, sealing said airway tube for communication solely with the laryngeal inlet, sealing said evacuation tube solely to the sphinctral region; and reflectance-oximeter probe means carried by said second cuff formation and oriented to radiate into and to sense radiation reflected from within a localized portion of the posterior wall of the pharynx.

26. The artificial airway device of claim 25, in which said airway tube is relatively rigid and curved to follow the airway of a patient.

27. An artificial airway device to facilitate a patient's lung ventilation, comprising an airway tube, an evacuation tube, and a laryngeal mask at one end of said tubes, said mask being of generally elliptical configuration extending from a proximal end to a distal end and in generally a single plane, said configuration being adapted for support by and around the laryngeal inlet and orienting the distal end of the airway tube at an angle to said plane and in substantial alignment with the axis of the laryngeal inlet when supported by and around the laryngeal inlet, the distal end of said mask having a first cuff formation configured for entry into and insertional location of said device by engagement with the upper sphinctral region of the oesophagus when the mask is Positioned for airway-tube alignment with the axis of the oesophagus inlet, said evacuation tube having an open distal end centrally within and axially short of the distal end of said first cuff formation, a second inflatable-cuff formation carried by said mask on the posterior side of said plane, inflation-passage means communicating with both said cuff formations, and reflectance-oximeter probe means carried by said second cuff formation and oriented to radiate into and to sense radiation reflected from within a localized portion of the posterior wall of the pharynx.

28. An artificial airway device to facilitate a patient's lung ventilation, comprising an airway tube, a suction tube, and a laryngeal mask at one end of said tubes, said mask having a proximal end and a distal end and being configured to form a seal of said airway tube solely around the circumference of the patient's laryngeal inlet, said distal end being configured for entry into and insertional location of said device at the entrance of the upper sphinctral region of the oesophagus when said Mask is positioned for sealing the airway tube to the laryngeal inlet, said evacuation tube having an open distal end centrally within but axially short of the distal end of said mask, and the distal end of said mask including a first inflatable flexible cuff formation for peripherally sealed engagement of the upper sphinctral region to the distal end of said evacuation tube, thus exposing a passage via said mask for airway-tube communication solely with the laryngeal inlet on the anterior side of said mask, while exposing the posterior side of said mask to the posterior wall of the pharynx, a second inflatable-cuff formation carried by the posterior side of said mask for inflated engagement to the posterior wall of the pharynx, inflation-passage means communicating with both said cuff formations, and reflectance-oximeter probe means carried by said second cuff formation and oriented to radiate into and to sense radiation reflected from within a localized portion of the posterior wall of the pharynx.

* * * * *